United States Patent [19]

Gilman et al.

[11] Patent Number: 4,816,464

[45] Date of Patent: Mar. 28, 1989

[54] 10-SUBSTITUTED BENZO[B][1,6]NAPHTHYRIDINES AS INHIBITORS OF INTERLEUKIN 1

[75] Inventors: Steven C. Gilman, Berwyn; Jerauld S. Skotnicki, Chadds Ford, both of Pa.

[73] Assignee: American Home Products Corporation, New York, N.Y.

[21] Appl. No.: 65,211

[22] Filed: Jun. 22, 1987

[51] Int. Cl.[4] .............................................. A61K 31/44
[52] U.S. Cl. ..................................................... 514/299
[58] Field of Search ........................................ 514/299

[56] References Cited
U.S. PATENT DOCUMENTS 3,674,790  7/1972  Wolf et al. ..................... 260/286 R Primary Examiner—Stanley J. Friedman
Attorney, Agent, or Firm—George Tarnowski

[57] ABSTRACT

There is disclosed a method for the treatment of inflammatory conditions and of collagenase-induced tissue destruction which comprises the administration of a therapeutically effective amount of a compound of the formula

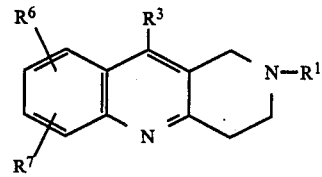

wherein
$R^1$ is lower alkyl or lower alkenyl or any of the foregoing optionally substituted with fluoro, carboxy, lower alkoxycarbonyl, $OR^2$, $N(R^2)_2$, $SR^2CON(R^2)_2$, $SO_2R^2$, cyano, nitro or trifluoromethyl;
$R^2$ is hydrogen, lower alkyl or phenyl;
$R^3$ is halo, morpholino, 4-methylpiperazino, $R^4NNHR^5$, $NR^4R^5$, $OR^5$, $SR^5$, $R^4NCH_2CH_2OCH_3$, $SCH_2CH_2CH_2NH_2$ or

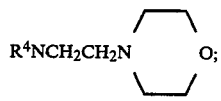

$R^4$ is hydrogen or lower alkyl;
$R^5$ is hydrogen, lower alkyl, lower alkanoyl, lower cycloalkyl or phenyl; and
$R^6$ and $R^7$ are each independently, hydrogen, halo, nitro, lower alkoxy, lower alkyl or trifluoromethyl;
which compounds, by virtue of their ability to inhibit interleukin 1, are useful as antiinflammatory agents and in treatment of disease states involving enzymatic tissue destruction, and are also intermediates in the preparation of other compounds which possess identical activities.

20 Claims, No Drawings

10-SUBSTITUTED BENZO[B][1,6]NAPHTHYRIDINES AS INHIBITORS OF INTERLEUKIN 1

This invention relates to a method for treating inflammation by the use of compounds possessing interleukin 1 (IL 1) antagonist activity and having antiinflammatory activity.

Interleukin 1 (IL 1) is a peptide hormone exhibiting a number of immune and inflammatory actions [Dinarello, *Rev. Inf. Dis.* 6, 51 (1984)]. IL 1 is produced, in response to inflammatory stimuli, by leukocytes such as macrophages and polymorphonuclear cells, as well as by a variety of other cell types such as synovial cells, endothelial cells and keratinocytes, and it mediates several biological responses of leukocytes on other tissue targets such as bone, articular joints, liver, hypothalamus, and brain.

IL 1 was originally shown to augment the proliferation of T lymphocytes for which it was named lymphocyte activating factor (LAF), and is believed to be important for the generation of T cell-dependent immune responses.

There is evidence to suggest a relationship between IL 1 and pathology in various diseases, particularly immunoinflammatory disorders such as rheumatoid arthritis [Dinarello et al., *Ann. Rev. Med.* 37, 173 (1986)]. IL 1 induces acute inflammatory responses producing soft tissue swelling (edema and erythema) [Granstein et al., *J. Clin. Invest.*, 77, 1010 (1986)]. It is a chemoattractant for polymorphonuclear leukocytes (PMN) and induces the activation and migration of these cells into tissues. IL 1 also stimultates the production of prostaglandin $E_2$, a potent inflammatory arachidonic acid metabolite, by a variety of cells and tissues including chondrocytes and synovial cells [Mizel et al., *Proc. Nat'l. Acad. Sci.*, 78, 2474 (1981) and Chang et al., *J. Immunol.*, 136, 1282 (1986)] and hypothalamic tissue. This effect on the hypothalamus is though to be responsible for fever production. IL 1 can induce articular joint destruction by stimulating the production of a variety of hydrolytic enzymes (neutral proteases such as collagenase, glycosaminoglycanases, etc.) which degrade cartilage matrix proteins (collagen, proteoglycan, etc.) by synovial cells, chondrocytes, and fibroblasts [Dayer et al., *Science*, 195, 191 (1977) and Postlethwaite et al., *J. Exp. Med.*, 157, 801 (1983)]. Furthermore, IL 1 induces hyperproliferation of dermal and synovial fibroblasts and is a potent inducer of bone resorption [Wood et al., *J. Immunol.*, 134, 895 (1985) and Gilman and Kimball, *Agents and Actions*, 16, 468 (1985)].

Finally, IL 1 mediates acute phase reactions includng alterations in plasma divalent cations, increased synthesis by liver cells of acute phase proteins (C-reactive protein, serum amyloid A, etc.) and fever. Accordingly, compounds which have IL 1 antagonist activity and thereby inhibit the biological effects of IL 1 can be advantageously used to block pathologies in which one or more of these events occur such as rheumatoid arthritis, osteoarthritis and related disorders [Rodnan and Schumacher, eds, "Primer on the Arthritic Diseases" 8 ed. Atlanta, 1983], psoriasis and other inflammatory/-proliferative skin disorders as well as diseases in which the secretion of collagenase (and other tissue hydrolysing neutral proteinases) has been implicated as a causative factor, including periodontal disease, tumor invasiveness, and epidermolysis bullosa [Perez-Tamayo, *Amer. J. Pathol.*, 92, 509 (1978) and Harris and Krane, *N. Engl. J. Med.*, 291, 652 (1974)] and so forth.

It has now been found that certain 10-substituted benzo[b][1,6]naphthyridines antagonize the activity of IL 1, and so are useful as antiinflammatory agents and in the treatment of pathologies whose etiology is collagenase-based tissue destruction. Some of the compounds used in the present invention are disclosed in U.S. Pat. Nos. 3,637,706 and 3,674,790 wherein these compounds are taught to be pharmacologically active, inter alia, as central nervous system depressants.

The present invention is directed to a method for the treatment of inflammatory conditions and of collagenase-induced tissue destruction which comprises the administration of a therapeutically effective amount of a compound having the formula:

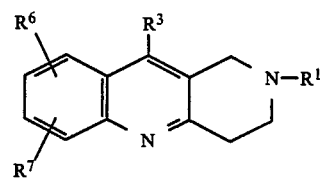

wherein
$R^1$ is lower alkyl or lower alkenyl or any of the foregoing optionally substituted with fluoro, carboxy, lower alkoxycarbonyl, $OR^2$, $N(R^2)_2$, $SR^2$, $CON(R^2)_2$, $SO_2R^2$, cyano, nitro or trifluoromethyl;.
$R^2$ is hydrogen, lower alkyl or phenyl;
$R^3$ is halo, morpholino, 4-methylpiperazino, $R^4NNHR^5$, $NR^4R^5$, $OR^5$, $SR^5$, $R^4NCH_2CH_2OCH_3$, $SCH_2CH_2CH_2NH_2$ or

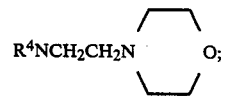

$R^4$ is hydrogen or lower alkyl;
$R^5$ is hydrogen, lower alkyl, lower alkanoyl, lower cycloalkyl or phenyl; and
$R^6$ and $R^7$ are each independently, hydrogen, halo, nitro, lower alkoxy, lower alkyl or trifluoromethyl.

The terms "lower alkyl", "lower alkenyl" and "lower alkoxy" refer to straight or branched chain moieties having 1 to 6 carbon atoms. The term "lower alkanoyl" refers to the moiety RCO— wherein R is a straight or branched chain alkyl group having 1 to 6 carbon atoms. The term "lowercycloalkyl" refers to a saturated ring having 4 to 7 carbon atoms. The term "halo" refers to fluoro, chloro and bromo.

The compounds of the invention can be prepared by the reaction of 1,4-dioxa-8-azaspiro[4.5]decane with a suitable halo-$R^1$ reactant, and following ketal hydrolysis, the reaction of the resultant intermediate with a suitably substituted amino benzoic acid in the presence of a halogenating agent to yield an intermediate halogenated benzo[b][1,6]naphthyridine:

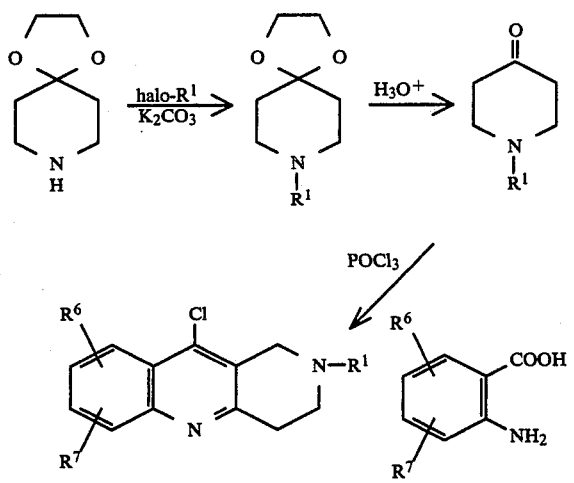

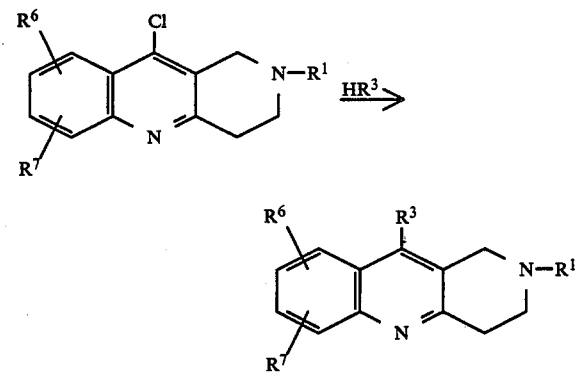

In the final step, the intermediate halogenated benzo[b][1,6]naphthyridine is reacted with a suitably substituted $R^3$-containing reactant to yield the desired final product:

The starting materials used in the above outlined preparative sequences are all available commercially or can be prepared by conventional methods disclosed in the chemical literature.

The compounds used in the method of the invention, by virtue of the ability to antagonize interleukin 1, are useful in the treatment of such diseases as rheumatoid arthritis, osteoarthritis, tendinitis, bursitis and similar conditions involving inflammation, as well as psoriasis and other inflammatory/proliferative skin disorders. Moreover, the compounds are useful in treating disease states involving enzymatic tissue destruction, for example, conditions in which collagenase has been implicated as a causative factor, such as rheumatoid arthritis joint destruction, periodontal disease, tumor invasiveness, corneal ulcerations, epidermolysis bullosa and the like.

When the disclosed compounds are employed in the method of the invention as antiinflammatory agents, or collagenase inhibitors, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For topical administration, the compounds may be formulated in the form of dusting powders, solutions, creams, lotions or aerosols in pharmaceutically acceptable vehicles, which are applied to affected portions of the skin.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The interleukin 1 antagonist activity, as well as the antiinflammatory effects of the compounds used in the method of the invention may be demonstrated by standard pharmacological procedures, which are described more fully in the examples given hereinafter.

These procedures illustrate the ability of the compounds used in the invention to inhibit the IL 1-induced release of neutral protease from articular chondrocytes; and measure the in vivo antiinflammatory activity of the compounds in the rate carageenan paw edema assay.

The following examples show the preparation and pharmacological testing of compounds used in the invention.

EXAMPLE 1

2-Butyl-7,10-dichloro-1,2,3,4-tetrahydrobenzo[b][1,6-]naphthyridine

A. 8-butyl-1,4-dioxa-8-azaspiro[4.5]decane

To a mixture of 15 g (0.015 mol) of 1,4-dioxa-8-azaspiro[4.5]decane, 15.93 g (0.115 mol) of $K_2CO_3$, and 100 ml of acetonitrile is added drowpwise 11.25 ml (0.105 mol) of 1-bromobutane. The mixture is stirred overnight at room temperature and then at 65° C. for 2 hours. After cooling, the mixture is diluted with water and extracted with methylene chloride. The combined extracts are washed with brine, dried over $Na_2SO_4$, and concentrated in vacuo to yield 16.63 g (80%) of the title compound as a yellow liquid: IR (neat) 2959 and 1092 $cm^{-1}$; NMR ($CDCl_3$)δ3.97 (s, 4H), 2.56 (s, 4H), 2.38 (m, 2H), 1.77 (t, 4H), 1.49 (m, 2H), 1.34 (m, 2H), 0.92 (t, 3H).

B. 1-Butyl-4-piperidinone

A mixture of 16.53 g (0.0829 mol) of the compound of A, above, and 250 ml of a 20% sulfuric acid/tetrahydrofuran (2:1) solution is allowed to stand at room temperature for 3 days and then stirred at 65° C. overnight.

The mixture is diluted with water, made basic with sodium hydroxide, and extracted with methyl chloride. The combined extracts are washed with brine, dried over Na$_2$SO$_4$, and concentrated in vacuo to furnish 11.16 g (87%) of title compound as a gold liquid: IR (neat) 2970 and 1725 cm$^{-1}$; NMR (CDCl$_3$)δ2.77 (t, 4H), 2.47 (m, 6H), 1.46 (m, 4H), 0.96 (t, 3H).

C

2-Butyl-7,10-dichloro-1,2,3,4-tetrahydrobenzo[b][1,6-]naphthyridine

To a slurry of 11.76 g (0.0685 mol) of 2-amino-4-chlorobenzoic acid and 57.5 ml of phosphorous oxychloride is added dropwise 10.64 g (0.0685 mol) of the compound of B, above. The mixture is stirred at reflux for 3 hours and then concentrated in vacuo. The residue is dissolved in chloroform and added slowly to an ice-NH$_4$OH mixture. The mixture is stirred for ½ hour and extracted with chloroform. The combined extracts are washed with water, dried over Na$_2$SO$_4$, and concentrated in vacuo to yield 23.06 g of a dark solid. purification by HPLC (twice) affords 2.59 g (12%) of title compound as a brown oil: IR (Neat) 2960, 1740, 1610, and 1478 cm$^{-1}$; NMR (CDCl$_3$)δ8.11 (d, 1H), 8.01 (s, 1H), 7.51 (m, 1H), 3.87 (s, 2H), 3.25 (t, 2H), 2.92 (t, 2H), 2.65 (m, 2H), 1.64 (m, 2H), 1.42 (m, 2H), 0.96 (t, 3H).

Analysis for: C$_{16}$H$_{18}$Cl$_2$N$_2$, Calculated: C, 62.14; H, 5.87; N, 9.06. Found: C, 61.35; H, 5.72; N, 9.15.

EXAMPLE 2

7,10-dichloro-1,2,3,4-tetrahydro-2-octylbenzo[b][1,6-]naphthyridine

A. 8-Octyl-1,4-dioxa-8-azaspiro[4.5]decane

To a mixture of 15 g (0.105 mol) of 1,4-dioxa-8-azaspiro[4.5]decane, 15.93 g (0.115 mol) of K$_2$CO$_3$, and 100 ml of acetonitrile is added dropwise 18.92 ml (0.105 mol) of iodooctane. The mixture is stirred overnight at room temperature and then at 65° C. for 2 hours. After cooling, the mixture was diluted with water and extracted with methylene chloride. The combined extracts are washed with brine, dried over Na$_2$SO$_4$, and concentrated in vacuo. The residue is triturated with ether and filtered. The filtrate is concentrated in vacuo to yield 24.04 g (90%) of title compound as a clear oil: IR (neat) 2925 and 1094 cm$^{-1}$; NMR (CDCl$_3$) δ3.97 (s, 4H), 2.56 (br, 4H), 2.38 (m, 2H), 1.78 (m, 4H), 1.51 (br, 2H), 1.28 (s, 10H), 0.89 (m, 3H).

B. 1-Octyl-4-piperidinone

A mixture of 23.9 g (0.0936 mol) of the compound of A, above, and 350 ml of a 10% sulfuric acid/tetrahydrofuran (2:1) solution is stirred at 65° C. for 4 hours, allowed to stand at room temperature for 3 days, then was stirred at 65° C. overnight. The mixture is diluted with water, made basic with sodium hydroxide, and extracted with methylene chloride. The combined extracts are washed with brine, dried over Na$_2$SO$_4$, and concentrated in vacuo to yield 4.65 g (24%) of a reddish liquid: IR (neat) 2930 and 1725 cm$^{-1}$; NMR (CDCl$_3$) δ2.76 (t, 4H), 2.46 (t, 6H), 1.32 (m, 12H), 0.89 (t, 3H).

C. 7,10-Dichloro-1,2,3,4-tetrahydro-2-octylbenzo[b][1,6-]naphthyridine

To a slurry of 3.613 g (0.021 mol) of 2-amino-4-chlorobenzoic acid and 17.66 ml of phosphorous oxychloride is added dropwise 4.45 g (0.021 mol) of the compound of B, above. The mixture is heated at reflux for 2 hours and then concentrated in vacuo. The residue is dissolved in chloroform and added slowly to an ice-NH$_4$OH mixture. After stirring for 20 minutes, the mixture is extracted with chloroform. The combined extracts are washed with water, dried over Na$_2$SO$_4$, and concentrated in vacuo to yield 7.11 g of crude solid. The material is purified by HPLC (twice) to afford 3.53 g (46%) of title compound as an off-white solid: m.p. 54°–57° C.; IR (KBr) 2920, 1610, and 1475 cm$^{-1}$; NMR (CDCl$_3$) δ8.11 (d, 1H), 8.01 (s, 1H), 7.51 (m, 1H), 3.85 (s, 2H), 3.25 (t, 2H), 2.90 (t, 2H), 2.64 (m, 2H), 1.31 (m, 10H), 0.87 (t, 3H).

Analysis for: C$_{20}$H$_{26}$Cl$_2$N$_2$, Calculated: C, 65.75; H, 7.17; N, 7.67. Found: C, 65.56; H, 7.19; N, 8.03.

EXAMPLE 3

7,10-Dichloro-1,2,3,4-tetrahydro-2-(2-propenyl)benzo[b][1,6]naphthyridine

A. 8-(2-Propenyl)-1,4-dioxa-8-azaspiro[4,5]decane

To a mixture of 15 g (0.015 mol) of 1,4-dioxa-8-azaspiro[4.5]decane, 15.93 g (0.115 mol) of K$_2$CO$_3$, and 100 ml of acetonitrile is added dropwise 9.07 ml (0.105 mol) of ;b 3-bromopropene. The mixture is stirred overnight at room temperature and then at 65° C. for 2 hours. After cooling, the mixture is diluted with water and extracted with methylene chloride. The combined extracts are washed with brine, dried over Na$_2$SO$_4$, and concentrated in vacuo to afford 9.48 g (49%) of title compound as an oil: ir (neat) 2955 and 1090 cm$^{-1}$; NMR (CDCl$_3$) δ5.91 (m, 1H), 5.21 (m, 2H), 3.97 (s, 4H), 3.05 (d, 2H), 2.56 (t, 4H), 1.76 (t, 4H).

B. 1-(2-Propenyl)-4-piperidinone

A mixture of 9.37 g (0.0511 mol) of the compound of A, above, and 150 ml of a 10% sulfuric acid/tetrahydrofuran (2:1) solution is stirred at 65° C. for 4 hours, allowed to stand at room temperature for 3 days, then stirred at 65° C. overnight. The mixture is diluted with water, made basic with sodium hydroxide, and extracted with methylene chloride. The combined extracts are washed with brine, dried over Na$_2$SO$_4$, and concentrated in vacuo to yield 5.63 g (79%) of a reddish liquid. IR (neat) 1720 cm$^{-1}$; NMR (CDCl$_3$) δ5.96 (m, 1H), 5.26 (m, 2H), 3.15 (d, 2H), 2.78 (t, 4H), 2.48 (t, 4H).

C. 7,10-Dichloro-1,2,3,4-tetrahydro-2-(2-propenyl)benzo[b][1,6]naphthyridine To a slurry of 6.164 g (0.0359 mol) of 2-amino-4-chlorobenzoic acid and 30.14 ml of phosphorous oxychloride is added dropwise 5.0 g (0.0359 mol) of the compound of B, above. The mixture is stirred under reflux for 3 hours and then concentrated in vacuo. The residue is taken up in chloroform and added slowly to an ice-NH$_4$OH mixture. After stirring for 20 minutes, the mixture is extracted with chloroform. The combined extracts are washed with brine, dried over Na$_2$SO$_4$, and concentrated in vacuo to yield 10.37 g of a black oil. Purification by HPLC affords 4.63 g of dark solid which is dissolved in ether, filtered, and concentrated in vacuo. Recrystallization from hexanes furnishes 3.045 g (29%) of title compound as a brown solid: m.p. 75°–77° C.; IR (KBr) 1602 cm$^{-1}$; NMR (CDCl$_3$) δ8.13 (d, 1H), 8.03 (s, 1H), 7.54 (m, 1H), 6.01 (m, 1H), 5.34 (m, 2H), 3.89 (s, 2H), 3.31 (m, 4H), 2.95 (t, 2H).

Analysis for: $C_{15}H_{14}Cl_2N_2$, Calculated: C, 61.44; H, 4.81; N, 9.56. Found: C, 61.45; H, 4.96; N, 9.50.

EXAMPLE 4

7,10-Dichloro-1,2,3,4-tetrahydro-2-(4-pentenyl)benzo[b][1,6]naphthyridine

A. 8-(4-Pentenyl)-1,4-dioxa-8-azaspiro[4.5]decane

To a mixture of 15 g (0.105 mol) of 1,4-dioxa-8-azaspiro[4.5]decane, 15.93 g (0.115 mol) of $K_2CO_3$, and 100 ml of acetonitrile is added dropwise 14.41 ml (0.105 mol) of 5-bromopentene. The mixture is stirred overnight at room temperature and then at 65° C. for 2 hours. After cooling, the mixture is diluted with water and extracted with methylene chloride. The combined extracts are washed with brine, dried over $Na_2SO_4$, and concentrated in vacuo to furnish 18.62 g (84%) of title compound as an oil: IR (neat) 2940 and 1090 cm$^{-1}$; NMR (CDCl$_3$) δ5.84 (m, 1H), 5.02 (m, 2H), 3.96 (s, 4H), 2.70–1.40 (m, 14H).

B. 1-(4-Pentenyl)-4-piperidinone

A mixture of 18.51 g (0.088 mol) of the compound of A, above, and 275 ml of a 10% sulfuric acid/tetrahydrofuran (2:1) solution is stirred at 65° C. for 4 hours, allowed to stand at room temperature for 3 days, then is stirred at 65° C. overnight. The mixture is diluted with water, made basic with sodium hydroxide, and extracted with methylene chloride. The combined extracts are washed with brine, dried over $Na_2SO_4$, and concentrated in vacuo to yield 12.3 g (84%) of a reddish liquid. IR (neat) 2940, 1722, and 1357 cm$^{-1}$; NMR (CDCl$_3$) δ5.82 (m, 1H), 5.03 (m, 2H), 2.57 (t, 4H), 2.48 (m, 6H), 2.14 (q, 2H), 1.67 (q, 2H).

C. 7,10-Dichloro-1,2,3,4-tetrahydro-2-(4-pentenyl)benzo[b][1,6]naphthyridine To a slurry of 12.054 g (0.070 mol) of 2-amino-4-chlorobenzoic acid and 58.9 ml of phosphorous oxychloride, is added dropwise 11.75 g (0.070 mol) of the compound of B, above. The mixture is stirred under reflux for 3 hours and concentrated in vacuo. The residue is dissolved in chloroform and slowly added to an ice-NH$_4$OH mixture. After stirring for 20 minutes, the mixture is extracted with chloroform. The combined extracts are washed with brine, dried over $Na_2SO_4$, and concentrated in vacuo to afford 22.42 g of a black oil. Purification by HPLC (twice) furnished 9.89 g (44%) of title compound as a dark solid: IR (KBr) 1605 cm$^{-1}$; NMR (CDCl$_3$) δ8.12 (d, 1H), 8.01 (s, 1H), 7.52 (m, 1H), 5.88 (m, 1H), 5.05 (m, 2H), 3.88 (s, 2H), 3.26 (t, 2H), 2.93 (t, 2H), 2.67 (m, 2H), 2.17 (m, 2H), 1.77 (m, 2H).

Analysis for: $C_{17}H_{18}Cl_2N_2$. Calculated: C, 63.56; H, 5.65; N, 8.72. Found: C, 62.85; H, 5.61; N, 8.64.

EXAMPLE 5

7,10-Dichloro-1,2,3,4-tetrahydro-2-methylbenzo[b][1,6]naphthyridine

1-Methyl-4-piperidone (66.0 g, 0.58 m) is slowly added to a slurry of 4-chloroanthranilic acid (100.0 g., 0.58 m) in phosphorous oxychloride (500 ml) and the resulting mixture refluxed for two hours. The solvent is evaporated and the residue taken up in methylene chloride (2 liters). This is slowly added to a stirred ammonium hydroxide—ice solution (10 liters). The methylene chloride solution is washed with water, dried over anhydrous sodium sulfate and evaporated giving 139.0 g of a green solid. This solid is extracted with 1.5 l of hexane, treated with charcoal, is concentrated and crystallized giving 79.0 g (49%) of crude product. Recrystallization from hexane gives a yellow crystalline solid, m.p. 114°–115° C.

analysis for: $C_{13}H_{12}Cl_2N$. Calculated: C, 58.46; H, 4.53; N, 10.49. Found: C, 58.63; H, 4.28; N, 10.23.

EXAMPLE 6

8,10-Dichloro-1,2,3,4-tetrahydro-2-methylbenzo[b][1,6]naphthyridine

1-Methyl-4-piperidone (130.0 g, 1.15 m), 5-chloroanthranillic acid (200.0 g, 1.16 m) and phosphorous oxychloride (800 ml) are allowed to react in a manner similar to Example 5. The crude product is extracted several times with hot hexane. The combined extracts are concentrated and the product is allowed to crystallize giving 140 g (45%) of solid. Recrystallization of the crude product from hexane gives a crystalline solid, m.p. 88°–89° C.

Analysis for: $C_{13}H_{12}Cl_2N_2$. Calculated: C, 58.46; H, 4.53; N, 10.49. Found: C, 58.51; H, 4.31; N, 10.38.

EXAMPLE 7

1-(7-Chloro-1,2,3,4-tetrahydro-2-methylbenzo[b][1,6]-naphthyridin-10-yl)-2-phenylhydrazine A solution of 2 g (7.49 mmol) of the compound of Example 5, 1.6 ml (16.3 mmol) of phenylhydrazine, 1.25 ml of concentrated hydrochloric acid, and 75 ml of absolute ethanol is stirred under reflux for 6 hours. The precipitate, on cooling, is collected and dissolved in methanol. Treatment of the solution with a $Na_2CO_3$ solution forms a precipitate which is collected and washed with water to furnish 1.448 g (57.1%l) of title compound as a tan solid: m.p. 175°–178° C.; IR (KBr) 3290, 1605, 1558, and 1486 cm$^{-1}$; NMR (CDCl$_3$) δ8.23 (d, 1H), 7.87 (s, 1H), 7.25 (m, 3H), 6.90 (m, 3H), 6.20 (s, 2H), 3.63 (s, 2H), 3.16 (t, 2H), 2.78 (t, 2H), 2.46 (s, 3H).

Analysis for: $C_{19}H_{19}ClN_4$. Calculated: C, 67.35; H, 5.65; N, 16.54. Found: C, 67.06; H, 5.83; N, 16.14.

EXAMPLE 8

2-Butyl-7-chloro-1,2,3,4-tetrahydro-10-(2-phenylhydrazino)benzo[b][1,6]naphthyridine A mixture of 1 g (3.23 mmol) of the compound of Example 1, 0.70 ml (7.11 mmol) of phenylhydrazine, 0.75 ml of concentrated hydrochloric acid, and 30 ml of absolute ethanol is stirred under reflux for 6 hours. The precipitate, on cooling, is collected and dissolved in methanol. Treatment with a $Na_2CO_2$ solution yields 0.625 g of an off-white solid after the precipitate is filtered and washed with water. Recrystalization from benzene/hexanes furnishes 0.355 g (29%) of title compounds as a white solid: m.p. 118°–120° C.; IR (KBr) 3230, 1608, and 1557 cm$^{-1}$; NMR (CDCl$_3$) δ8.28 (d, 1H), 7.93 (s, 1H), 7.30 (m, 3H), 6.96 (m, 3H), 6.22 (s, 1H), 3.72 (s, 2H), 3.19 (t, 2H), 2.84 (t, 2H), 2.56 (m, 2H), 1.53 (m, 2m), 1.36 (m, 2H), 0.91 (t, 3H).

Analysis for: $C_{22}H_{25}ClN_4$. Calculated: C, 69.37; H, 6.62; N, 14.71. Found: C, 67.27; H, 6.91; N, 14.91.

EXAMPLE 9

7-Chloro-1,2,3,4-tetrahydro-2-octyl-10-(2-phenylhydrazino)benzo[6][1,6]naphthyridine A mixture of 1 g (2.74 mmol) of the compound of Example 2, 0.593 ml (6.02 mmol) of phenylhydrazine, 0.75 ml of concentrated hydrochloric acid, and 30 ml of absolute ethanol is stirred under reflux for 6 hours. The precipitate, on cooling, is collected and dissolved in methanol. Treatment with $Na_2CO_3$ solution results in a precipitate which is filtered and washed with water to furnish 0.880 g of a light yellow solid. Recrystallization from benzene/hexanes affords 0.422 g (35%) of title compound as a white solid: m.p. 109°–112° C.; IR (Kbr) 3220, 1609, and 1563 $cm^{-1}$; NMR ($CDCl_3$)δ8.25 (d, 1H), 7.91 (s, 1H), 7.28 (m, 3H), 6.94 (m, 3H), 6.25 (s, 1H), 3.70 (s, 2H), 3.18 (t, 2H), 2.83 (t, 2H), 2.54 (m, 2H), 1.53 (br, 2H), 1.26 (m, 10H), 0.88 (t, 3H).

Analysis for: $C_{26}H_{33}ClN_4$. Calculated: C, 71.45; H, 7.61; N, 12.82. Found: C, 69.95; H, 7.91; N, 12.26.

EXAMPLE 10

7-Chloro-1,2,3,4-tetrahydro-10-(2-phenylhydrazino)-2-(2-propenyl)benzo[b][1,6]naphthyridine, dihydrate A mixture of 1 g (3.4 mmol) of the compound of Example 3, 0737 ml (7.49 mmol) of phenylhydrazine, 0.75 ml of concentrated hydrochloric acid, and 30 ml of absolute ethanol is stirred under reflux for 6 hours. The precipitate is collected then dissolved in methanol and treated with a $Na_2CO_3$ solution. The precipitate is collected and washed with water to yield 0.916 g of a yellow solid. Recrystallization from benzene/hexanes furnishes 0.731 g (59%) of title compound as an off-white solid: m.p. 138°–140° C.; IR (KBr) 3260, 1610, and 1560 $cm^{-1}$; NMR ($CDCl_3$) δ8.28 (d, 1H), 7.93 (2, 1H), 7.29 (m, 3H), 6.93 (m, 3H), 6.29 (s, 1H), 5.93 (m, 1H), 5.21 (m, 2H), 3.70 (s, 2H), 3.20 (m, 4H), 2.84 (t, 2H).

Analysis for: $C_{21}H_{21}ClN_4 \cdot 2H_2O$. Calculated: C, 62.91; H, 6.29; N, 13.98. Found: C, 63.79; H, 5.81; N, 13.96.

EXAMPLE 11

7-Chloro-1,2,3,4-tetrahydro-2-(4-pentenyl)-10-(2-phenyl-hydrazino)benzo[b][1,6]naphthyridine, sesquihydrate A mixture of 1 g (3.11 mmol) of the compound of Example 4, 0674 ml (6.85 mmol) of phenylhydrazine, 0.75 ml of concentrated hydrochloric acid, and 30 ml of absolute ethanol is stirred under reflux for 6 hours. On cooling, the precipitate is collected and dissolved in methanol. Treatment with a $Na_2CO_3$ solution forms a precipitate which is collected and washed with water to yield 1.495 g of an off-white solid. Recrystallization from benzene/hexanes furnishes 0.818 g (67%) of title compound as a gold solid: m.p. 97°–100° C.; IR (KBr) 3245, 1610, and 1562 $cm^{-1}$; NMR ($CDCl_3$) δ8.27 (d, 1H), 7.92 (s, 1H), 7.29 (m, 3H), 6.94 (m, 3H), 6.22 (s, 1H), 5.83 (m, 1H), 5.02 (m, 2H), 3.70 (s, 2H), 3.18 (t, 2H), 2.83 (t, 2H), 2.56 (m, 2H), 2.10 (m, 2H), 1.64 (m, 2H).

Analysis for: $C_{23}H_{25}ClN_4 \cdot 1\frac{1}{2}H_2O$ Calculated: C, 65.78; H, 6.72; N, 13.34. Found: C, 65.54; H, 6.45; N, 13.18.

EXAMPLE 12

7-Chloro-1,2,3,4-tetrahydro-N-(2-methoxyethyl)-2-methylbenzo[b]-[1,6]naphthyridin-10-amine, three quarter hydrate A mixture of 0.6 g (2.25 mmol) of the compound of Example 5 and 0.425 g of phenol is heated at 100° C. for 15 minutes. To the mixture is added 1.173 ml (13.5 mmol) of 20 methoxyethylamine and the resulting mixture is stirred at 100° C. for 2 days. The mixture is taken up in methylene chloride and washed with a 20% potassium hydroxide solution, dried over $Na_2SO_4$, and concentrated in vacuo to yield 1.3 g of a dark oil. Purification by HPLC and trituration with ether furnishes 0.139 g (20%) of title compound as a dark solid: IR (neat) 3380 and 1610 $cm^{-1}$; NMR ($CDCl_3$) δ7.96 (m, 2H), 7.35 (m, 1H), 4.66 (m, 1H), 3.64 (s, 2H), 3.62 (m, 2H), 3.53 (m, 2H), 3.43 (s, 3H), 3.24 (t, 2H), 2.85 (t, 2H), 2.57 (s, 3H).

Analysis for: $C_{16}H_{20}ClN_3O \cdot \frac{3}{4}H_2O$. Calculated: C, 60.18; H, 6.78; N, 13.16. Found: C, 60.31; H, 6.41; N, 12.76.

EXAMPLE 13

7-Chloro-1,2,3,4-tetrahydro-2-methyl-N-(2-(4-morpholinyl)-ethyl)benzo[b][1,6]naphthyridin-10-amine A mixture of 0.6 g (2.25 mmol) of the compound of Example 5 and 0.423 g (4.5 mmol) of phenol is stirred at 100° C. for 15 minutes under nitrogen. To the mixture is added 0.591 ml (4.5 mmol) of N-(2-aminoethyl)morpholine which is then stirred at 135° C. for 5 hours. After cooling, the mixture is taken up in methylene chloride and washed with a 20% potassium hydroxide solution. The solution is dried over $Na_2SO_4$, concentrated in vacuo and triturated with ethyl acetate to furnish 0.56 g of a yellow solid. Recrystallization from benzene/hexanes affords 0.470 g (58%) of title compound as yellow rodlike crystals: m.p. 143°–145° C.; IR (KBr) 3340, 1604, and 1113 $cm^{-1}$; NMR ($CDCl_3$) δ7.99 (m, 2H), 7.34 (m, 1H), 5.24 (br, 1H), 3.81 (m, 4H), 3.66 (s, 2H), 3.56 (m, 2H), 3.22 (t, 2H), 2.85 (t, 2H), 2.65 (t, 2H), 2.56 (m, 7H).

Analysis for: $C_{19}H_{25}ClN_4O$. Calculated: C, 63.23; H, 6.93; N, 15.53. Found: C, 63.90; H, 6.89; N, 15.83.

EXAMPLE 14

10-Anilino-7-chloro-1,2,3,4-tetrahydro-2-methylbenzo[b][1,6]naphthyridine

A mixture of the compound of Example 5 (5.0 g, 0.018 m) and 3.36 g (0.036 m) of phenol is heated under nitrogen at 100° C. for fifteen minutes until a clear melt is obtained. Aniline (3.3 ml, 0.036 m) is then added dropwise with stirring and the mixture is heated at 135°–140° C. for five hours. The reaction product is dissolved in methlene chloride and extracted with a 20% potassium hydroxide solution. After being dried over anhydrous sodium sulfate, the methylene chloride solution is evapotated, giving the free base. This product is triturated with ethyl acetate and recrystallized twice from acetonitrile giving 4.0 g (69%) of title compound as a crystaline solid, m.p. 197°–198° C.

Analysis for: $C_{19}H_{18}ClN_2$. Calculated: C, 70.47; H, 5.60; N, 12.98. Found: C, 70.40; H, 5.40; N, 12.72.

The compounds of Examples 15 and 16 are prepared in a manner similar to the procedure of Example 14:

EXAMPLE 15

7-Chloro-1,2,3,4-tetrahydro-2-methyl-10-phenoxybenzo[b][1,6]naphthyridine

A mixture of the compound of Example 5 (5.0 g, 0.018 m) and phenol (3.38 g, 0.036 m) is reacted to form the free base which is recrystallized three times from hexane to yield the title compound as a crystaline solid, m.p. 138°–139° C.

Analysis for: $C_{19}H_{17}ClN_2O$. Calculated: C, 70.25; H, 5.27; N, 8.64. Found: C, 70.50; H, 4.91; N, 8.87.

EXAMPLE 16

7-Chloro-1,2,3,4-tetrahydro-2-methyl-10-(4-methyl-1-piperazinyl)benzo[b][1,6]naphthyridine A mixture of the compound of Example 5 (8.0 g, 0.03 m), 5.65 g (0.06 m) of phenol and 7.0 g (0.07 m) of N-methylpiperazine is reacted to form the free base which is triturated with pentane and recrystallized from hexane giving the title compound as a crystalline solid, m.p. 114°–115° C.

Analysis for: $C_{19}H_{25}ClN_4$. Calculated: C, 65.33; H, 7.02; N, 16.94. Found: C, 65.74; H, 6.97; N, 16.79.

EXAMPLE 17

7-Chloro-1,2,3,4-tetrahydro-2-methyl-10-thiophenyl-benzo[b][1,6]naphthyridine

A solution of 5.0 g (0.018 m) of the compound of Example 5, 2.03 ml (0.02 m) of thiophenol, 1 ml of concentrated hydrochloric acid and 300 ml of 95% absolute ethanol is refluxed for four hours. After evaporation of the solution, the residue is dissolved in methylene chloride and extracted with a 20% aqueous sodium carbonate solution. After being dried over anhydrous sodium sulfate, the methylene chloride is evaporated and the residue is triturated with hexane. The crude product (5.2 g, 85%) is recrystallized twice from acetonitrile to give the title compound, m.p. 131°–132° C.

Analysis for: $C_{19}H_{17}ClN_2S$. Calculated: C, 66.94; H, 5.03; N, 8.22. Found: C, 67.21; H, 4.73; N, 8.11.

EXAMPLE 18

8-Chloro-1,2,3,4-tetrahydro-2-methyl-10-phenoxybenzo[b][1,6]naphthyridine

A mixture of the compound of Example 6 (5.0 g, 0.018 mol) and phenol (3.38 g, 0.036 mol) is reacted as described for Example 14 to obtain the free base which is recrystallized three times from hexane to afford the title compound as a crystalline solid, m.p. 182°–184° C.

Analysis for: $C_{19}H_{17}ClN_2O$. Calculated: C, 70.25; H, 5.27; N, 8.64. Found: C, 70.39; H, 5.07; N, 8.77.

EXAMPLE 19

10-Anilino-8-chloro-1,2,3,4-tetrahydro-2-methylbenzo[b][1,6]naphthyridine

By the method described for Example 14, a mixture of the compound of Example 6 (15.0 g, 0.0562 mol), 10.69 (0.115 mol) of phenol and 10.3 mol (0.115 mol) of aniline is reacted. Thereafter, the reaction mixture is slurried with a mixture of 10% aqueous potassium hydroxide and diethyl ether. The insoluble product is filtered and recrystallized from acetonitrile giving the title compound (13.0 g, 72%), m.p. 137°–139° C.

Analysis for: $C_{19}H_{13}ClN_3$. Calculated: C, 70.47; H, 5.60; N, 12.98. Found: C, 70.51; H, 5.40; N, 13.14.

EXAMPLE 20

(8-Chloro-1,2,3,4-tetrahydro-2-methylbenzo[b][1,6]naphthyridin-10-yl)hydrazine

A solution of 5.0 g (0.0188 mol) of the compound of Example 6, 3.5 g (0.074 m) of 95% hydrazine and 50 ml of n-propyl alcohol is refluxed for four hours. The solution is evaporated and the residue treated simultaneously with methylene chloride and a sodium carbonate solution leaving an insoluble solid (2.0 g, 41%). Recrystallization of the product from benzene affords the title compound as a crystalline solid, m.p. 172°–173° C.

Analysis for: $C_{12}H_{18}ClN_4$. Calculated: C, 59.44; H, 5.75; N, 21.23. Found: C, 59.20; H, 5.66; N, 21.31.

EXAMPLE 21

10-(3-Aminopropylthio)-8-chloro-1,2,3,4-tetrahydro-2-methylbenzo[b][1,6]naphthyridine A solution of 5.0 g (0.0188 mol) of the compound of Example 6, 3.3 g (0.02244 m) of 3-aminopropanethiol hydrochloride, 15 ml of 18.5% aqueous potassium hydroxide (0.05 m) and 30 ml of absolute ethanol is refluxed for one and a half hours. After evaporation of the solution, the residue is dissolved in methylene chloride and extracted with water. Evaporation of the methylene chloride solution gives the free base. Recrystallization of the product from hexane affords the title compound as a crystaline solid (3.2 g, 53%), m.p. 87°–89° C.

Analysis for: $C_{16}H_{20}ClN_3S$. Calculated: C, 59.70; H, 6.26; N, 13.05; S, 9.96. Found: C, 60.27; H, 6.40; N, 13.02; S, 9.95.

EXAMPLE 22

The ability of the compounds of the inventions to inhibit interleukin 1 is measured by the ability of the test compounds to inhibit the IL 1-induced release of neutral protease from rabbit articular chondrocytes.

This assay is carried out as follows:

Isolation of rabbit chondrocytes:

Male New Zealand White rabbits are anesthetized with 50 mg/kg of ketamine (i.m.) and killed by an intracardiac injection of 3 mls. of Nembutal. The knee joints of both legs are resected and the articular surfaces are exposed. Cartilage slices are obtained using a scalpel and are placed in a tissue culture dish (100 mm diameter) containing 10 mls of Hank's balanced salt solution (HBSS). The chondrocytes within the cartilage slices are then liberated by a series of enzyme digestions. The slices are incubated for 10 min. at 37° C. in 0.05% hyaluronidase (Sigma H-3884), rinsed with HBSS and incubated with 0.2% trypsin (Sigma T-2395) for 10 min. at 37° C. The slices are rinsed again and incubated for 10 mins. at 37° C. with 1.2% collagenase (Sigma C-5138). The slices are then rinsed again with HBSS and resuspended in 10 ml of Ham's F-12 medium containing 10% fetal bovine calf serum (FCS) and 0.2% collagenase and incubated overnight at 37° C. in a 5% $CO_2$ incubator. The next day, the medium containing the digested cartilage fragments and liberated chondrocytes is transferred to a 15 ml centrifuge tube and the cells are collected by centrifugation and washed twice and resuspended in Ham's F-12 medium. The cells are then plated into 24-well tissue culture plates ($2 \times 10^5$ cells/well) and incubated at 37° C. until confluent (usually 4–6 days).

Stimulation of chondrocytes and drug treatment:

The confluent chondrocytes are rinsed twice with serum-free Ham's F-12 medium and 1 ml is added to each well. Fifty $\mu$l of purified human IL 1 (100 Units/ml; Genzyme Corporation, Boston, MA) is then added to stimulate these cells to secrete neutral protease. To measure drug effects, the cells are treated with test compound 10 min. prior to addition of IL 1. The standard screening dose is 10 $\mu$M. Twenty-four hours after IL 1 stimulation, supernatant fluids are collected and assayed for neutral protease activity.

Neutral protease assay:

The neutral protease activity of chondrocyte supernatant fluids is determined by their ability to degrade an insoluble protease substrate, azocoll (Sigma). Supernatants are treated for 10 min. at room temperature with 350 μM p-aminophenylmurcuric acetate to activate the latent enzyme. Three hundred μl of supernatant is then mixed with 500 μl of a 20 mg/ml suspension of azocoll and incubated at 37° C. for 18-24 hrs. with gentle rocking. The mixtures are centrifuged and the amount of substrate hyrolyzed is determined by measuring the absorbance of the supernatant at 520 nm.

Drug effects are calculated as the % change in enzyme activity (absorbance) by supernatants from drug-treated chondrocytes relative to enzyme activity of supernatants from vehicle-treated chondrocytes as follows:

% Inhibition of Protease Secretion =

$$\frac{(A_{520})\text{ Untreated Supernatant} - A_{520}\text{ Drug Treated Supernatant}}{A_{520}\text{ Untreated Supernatant}} \times 100$$

Where tested in this assay, the compounds of the invention gave the following results:

| Compound of Exampe No. | Dose (μM) | % Inhibition (I.S.D.) |
|---|---|---|
| 1 | 10 | 3 ± 0 |
| 2 | 10 | 51 ± 0 |
| 4 | 10 | 12 ± 5 |
| 5 | 10 | 26 ± 23 |
| 6 | 10 | 13 ± 6 |
| 7 | 10 | 78 ± 13 |
|   | 1  | 35 ± 22 |
| 8 | 1 | 22 ± 6 |
| 9 | 1 | 22 ± 6 |
| 10 | 10 | 62 ± 2 |
| 11 | 10 | 11 ± 26 |
| 12 | 10 | 62 ± 28 |
| 13 | 10 | 4 ± 13 |
| 14 | 10 | 14 ± 4 |
| 15 | 10 | 22 ± 28 |
| 16 | 5 | 14 ± 3 |
| 17 | 10 | 44 ± 21 |
| 18 | 10 | 9 ± 28 |
| 19 | 10 | 23 ± 25 |
| 20 | 5 | 18 ± 0 |
| 21 | 10 | 42 ± 26 |

The results show that the compounds tested exhibit a moderate to quite significant inhibition of IL 1-induced protease secretion.

EXAMPLE 23

The compounds of the invention are tested in the rat carrageenan paw edema assay to determined their ability to inhibit the acute inflammatory response.

This assay is carried out as follows:

140-180 gm male Sprague-Dawley rats, in groups of 6 animals, are injected subcutaneously in the right paw with 0.1 ml of 1% carrageenan at zero time. Mercury plethysmographic readings (ml) of the paw are made at zero time and 3 hours later. Test compounds are suspended or dissolved in 0.5% methylcellulose and given perorally 1 hour prior to carrageenan administration.

The increase in paw volume (edema in ml.) produced by the carrageenan is measured. Paw edema is calculated (3 hour volume minus zero time volume), and percent inhibit of edema is determined. Unpaired Student's t-test is used to determine statistical significance.

The activity of standard drugs in this assay is as follows:

| Drug | Oral ED$_{50}$ (95% C.L.) mg/kg |
|---|---|
| Indomethacin | 3.7 (0.6, 23.8) |
| Aspirin | 145.4 (33.1, 645.6) |
| Phenylbutazone | 26.2 (2.3, 291.0) |

When tested in this assay, a compound of the invention gave the following results:

| Compound of Example No. | Dose (mg/kg) | % Change |
|---|---|---|
| 7 | 100 | 59 |
|   | 90 | 68 |
|   | 30 | 64 |
|   | 10 | 41 |

The results show that the compounds tested have activity in the rat carrageenan paw edema assay, evidencing an effect on the acute inflammatory response.

What is claimed:

1. A method for the treatment of inflammatory conditions and of collagenase-induced tissue destruction in warm-blooded animals which comprises the administration thereto of an anti-inflammatory/collagenase inhibitory amount of a compound having the formula

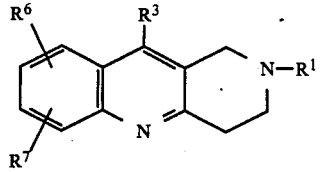

wherein
R$^1$ is lower alkyl or lower alkenyl or any of the foregoing optionally substituted with fluoro, carboxy, lower alkoxycarbonyl, OR$^2$, N(R$^2$)$_2$, SR$^2$, CON(R$^2$)$_2$, SO$_2$R$^2$, cyano, nitro or trifluoromethyl;
R$^2$ is hydrogen, lower alkyl or phenyl;
R$^3$ is halo, R$^4$NNHR$^5$, NR$^4$R$^5$, OR$^5$, SR$^5$, R$^4$NCH$_2$CH$_2$OCH$_3$ or SCH$_2$CH$_2$CH$_2$NH$_2$;
R$^4$ is hydrogen or lower alkyl;
R$^5$ is hydrogen, lower alkyl, lower alkanoyl, lower cycloalkyl or phenyl; and
R$^6$ and R$^7$ are each independently, hydrogen, halo, nitro, lower alkoxy, lower alkyl or trifluoromethyl 2. The method of claim 1, wherein the compound administered is 2-butyl-7,10-dichloro-1,2,3,4-tetrahydrobenzo[b][1,6]naphthyridine.

3. The method of claim 1, wherein the compound administered is 7,10-dichloro-1,2,3,4-tetrahydro-2-octylbenzo[b][1,6]naphthyridine.

4. The method of claim 1, wherein the compound administered is 7,10-dichloro-1,2,3,4-tetrahydro-2-(2-propenyl)benzo[b][1,6]naphthyridine.

5. The method of claim 1, wherein the compound administered is 7,10-dichloro-1,2,3,4-tetrahydro-2-(4-pentenyl)benzo[b][1,6]naphthyridine.

6. The method of claim 1, wherein the compound administered is 7,10-dichloro-1,2,3,4-tetrahydro-2-methylbenzo[b][1,6]naphthyridine.

7. The method of claim 1, wherein the compound administered is 8,10-dichloro-1,2,3,4-tetrahydro-2-methylbenzo[b][1,6]naphthyridine.

8. The method of claim 1, wherein the compound administered is 1-(7-chloro-1,2,3,4-tetrahydro-2-methylbenzo[b][1,6]naphthyridin-10-yl)-2-phenylhydrazine.

9. The method of claim 1, wherein the compound administered is 2-butyl-7-chloro-1,2,3,4-tetrahydro-10-(2-phenylhydrazino)benzo[b][1,6]naphthyridine.

10. The method of claim 1, wherein the compound administered is 7-chloro-1,2,3,4-tetrahydro-2-octyl-10-(2-phenylhydrazino)benzo[b][1,6]naphthyridine.

11. The method of claim 1, wherein the compound administered is 7-chloro-1,2,3,4-tetrahydro-10-(2-phenylhydrazino)-2-(2-propenyl)benzo[b][1,6]naphthyridine.

12. The method of claim 1, wherein the compound administered is 7-chloro-1,2,3,4-tetrahydro-2-(4-pentenyl)-10-(2-phenylhydrazino)benzo[b][1,6]naphthyridine.

13. The method of claim 1, wherein the compound administered is 7-chloro-1,2,3,4-tetrahydro-N-(2-methoxyethyl)-2-methylbenzo[b][1,6]naphthyridin-10-amine.

14. The method of claim 1, wherein the compound administered is 10-anilino-7-chloro-1,2,3,4-tetrahydro-2-methylbenzo[b][1,6]naphthyridine.

15. The method of claim 1, wherein the compound administered is 7-chloro-1,2,3,4-tetrahydro-2-methyl-10-phenoxybenzo[b][1,6]naphthyridine.

16. The method of claim 1, wherein the compound administered is 8-chloro-1,2,3,4-tetrahydro-2-methyl-10-phenoxybenzo[b][1,6]naphthyridine.

17. The method of claim 1, wherein the compound administered is 10-anilino-8-chloro-1,2,3,4-tetrahydro-2-methylbenzo[b][1,6]naphthyridine.

18. The method of claim 1, wherein the compound adminstered is (8-chloro-1,2,3,4-tetrahydro-2-methylbenzo[b][1,6]naphthyridin-10-yl)hydrazine.

19. The method of claim 1, wherein the compound administered is 10-(3-aminopropylthio)-8-chloro-1,2,3,4-tetrahydro-2-methylbenzo[b][1,6]naphthyridine.

20. The method of claim 1, wherein the compound administered is 7-chloro-1,2,3,4-tetrahydro-2-methyl-10-thiophenylbenzo[b][1,6]naphthyridine.

* * * * *